US00PP29861P2

(12) United States Plant Patent
Conibear

(10) Patent No.: US PP29,861 P2
(45) Date of Patent: Nov. 20, 2018

(54) LUPINE PLANT NAMED 'WCLKICA'

(50) Latin Name: ***Lupinus* hybrid**
Varietal Denomination: WCLKICA

(71) Applicant: Sarah Frances Conibear, Bideford (GB)

(72) Inventor: Sarah Frances Conibear, Bideford (GB)

( * ) Notice: Subject to any disclaimer, the term of this patent is extended or adjusted under 35 U.S.C. 154(b) by 0 days.

(21) Appl. No.: 15/731,491

(22) Filed: Jun. 19, 2017

(51) Int. Cl.
*A01H 5/02* (2018.01)

(52) U.S. Cl.
USPC ..... Plt./263.1

(58) Field of Classification Search
USPC ..... Plt./263.1
See application file for complete search history.

*Primary Examiner* — Anne Marie Grunberg
(74) *Attorney, Agent, or Firm* — C. A. Whealy

(57) ABSTRACT

A new and distinct cultivar of Lupine plant named 'WCLKICA', characterized by its upright plant habit; moderately vigorous to vigorous growth habit; numerous large violet blue and white bi-colored flowers arranged on dense terminal racemes; and good garden performance.

2 Drawing Sheets

Botanical designation: *Lupinus* hybrid.
Cultivar denomination: 'WCLKICA'.

BACKGROUND OF THE INVENTION

The present invention relates to a new and distinct cultivar of Lupine plant, botanically known as *Lupinus* hybrid and hereinafter referred to by the name 'WCLKICA'.

The new Lupine plant is a product of a planned breeding program conducted by the Inventor in Devon, United Kingdom. The objective of the breeding program is to develop new uniform and freely flowering Lupine plants with large attractive flowers.

The new Lupine plant originated from an open-pollination in June, 2012 of an unnamed selection of *Lupinus* Russell Hybrids, not patented, as the female, or seed, parent with an unknown selection of *Lupinus* hybrid as the male, or pollen, parent. The new Lupine plant was discovered and selected by the Inventor in June, 2012 as a single flowering plant within the progeny of the stated open-pollination in a controlled environment in Devon, United Kingdom.

Asexual reproduction of the new Lupine plant by in vitro meristem culture in a controlled greenhouse environment in Hillegom, The Netherlands since March, 2013 has shown that the unique features of this new Lupine plant are stable and reproduced true to type in successive generations of asexual reproduction.

SUMMARY OF THE INVENTION

Plants of the new Lupine have not been observed under all possible combinations of environmental conditions and cultural practices. The phenotype may vary somewhat with variations in environment such as temperature and light intensity without, however, any variance in genotype.

The following traits have been repeatedly observed and are determined to be the unique characteristics of 'WCLKICA'. These characteristics in combination distinguish 'WCLKICA' as a new and distinct Lupine plant:

1. Upright plant habit.
2. Moderately vigorous to vigorous growth habit.
3. Numerous large violet blue and white bi-colored flowers arranged on dense terminal racemes.
4. Good garden performance.

Plants of the new Lupine can be compared to plants of the female parent selection. Plants of the new Lupine differ from plants of the female parent selection primarily in the following characteristics:

1. Plants of the new Lupine are shorter than plants of the female parent selection.
2. Plants of the new Lupine are more vigorous and healthier than plants of the female parent selection.
3. Racemes of plants of the new Lupine are denser than racemes of plants of the female parent selection.

Plants of the new Lupine can be compared to plants of *Lupinus* hybrid 'The Governors', not patented. Plants of the new Lupine differ primarily from plants of 'The Governors' in the following characteristics:

1. Plants of the new Lupine are shorter than plants of 'The Governors'.
2. Plants of the new Lupine are more vigorous and healthier than plants of 'The Governors'.
3. Racemes of plants of the new Lupine are denser than racemes of plants of 'The Governors'.
4. Plants of the new Lupine and 'The Governors' differ in flower color as plants of 'The Governors' have dark blue purple and white bi-colored flowers.

BRIEF DESCRIPTION OF THE PHOTOGRAPHS

The accompanying colored photographs illustrate the overall appearance of the new Lupine plant showing the colors as true as it is reasonably possible to obtain in colored reproductions of this type. Colors in the photographs may differ slightly from the color values cited in the detailed botanical description which accurately describe the colors of the new Lupine plant.

The photograph on the first sheet is side perspective view of a typical flowering plant of 'WCLKICA' grown in a ground bed.

The photograph on the second sheet is a close-up view of a typical flowering plant of 'WCLKICA' grown in a ground bed.

DETAILED BOTANICAL DESCRIPTION

The aforementioned photographs and following observations, measurements and values describe plants of the new Lupine grown during the spring and early summer in ground beds in an outdoor nursery in Hillegom, The Netherlands and under cultural practices typical of commercial Lupine production. During the production of the plants, day temperatures ranged from 13° C. to 27° C. and night temperatures ranged from 5° C. to 18° C. Plants were one year old when the photographs and the detailed description were taken. In the detailed description, color references are made to The Royal Horticultural Society Colour Chart, 2015 Edition, except where general terms of ordinary dictionary significance are used.

Botanical classification: *Lupinus* hybrid 'WCLKICA'.

Parentage:

*Female, or seed, parent*.—Unnamed selection of *Lupinus* Russell Hybrids, not patented.

*Male, or pollen, parent*.—Unknown selection of *Lupinus* hybrid, not patented.

Propagation:

*Type*.—By in vitro meristem culture.

*Time to initiate roots, summer and winter*.—About four to five days at temperatures about 20° C.

*Time to produce a rooted young plant, summer*.—About five to six weeks at temperatures about 15° C. to 17° C.

*Time to produce a rooted young plant, winter*.—About seven to eight weeks at temperatures about 15° C. to 17° C.

*Root description*.—Thick, fleshy; typically creamy white to light brown in color, actual color of the roots is dependent on substrate composition, water quality, fertilizer type and formulation.

*Rooting habit*.—Main tap root with low lateral branching; medium in density.

Plant description:

*Plant and growth habit*.—Upright plant habit; moderately vigorous to vigorous growth habit and moderate growth rate.

*Branching habit*.—Freely basal branching habit.

*Plant height, soil level to top of floral plane*.—About 67.8 cm.

*Plant diameter* (*area of spread*).—About 47.1 cm.

Lateral branch description:

*Length*.—About 13 cm.

*Diameter*.—About 1.9 cm.

*Internode length*.—About 3.5 cm.

*Texture and luster*.—Sparsely to moderately pubescent; moderately glossy.

*Strength*.—Strong.

*Color*.—Close to 144B; proximally, strongly tinged with close to 187B to 187C.

Leaf description:

*Arrangement*.—Alternate, palmately compound with about 13 leaflets per leaf.

*Leaf length*.—About 16.9 cm.

*Leaf width*.—About 17 cm.

*Leaflet length*.—About 9.5 cm.

*Leaflet width*.—About 2.5 cm.

*Leaf shape*.—Palmate, orbicular in outline.

*Leaflet shape*.—Oblanceolate.

*Leaflet apex*.—Acute.

*Leaflet base*.—Cuneate.

*Leaflet margin*.—Entire.

*Leaflet texture and luster, upper surface*.—Smooth, glabrous; matte.

*Leaflet texture and luster, lower surface*.—Moderately pubescent; matte.

*Leaflet venation pattern*.—Pinnate.

*Leaflet color*.—Developing leaflets, upper surface: Close to 143A. Developing leaflets, lower surface: Close to 138A. Fully expanded leaflets, upper surface: Close to N137B; venation, close to 143B. Fully expanded leaflets, lower surface: Close to between 138A and 147B; venation, close to 144B.

*Leaf petioles*.—Length: About 17.3 cm. Diameter: About 5 mm. Texture and luster, upper and lower surfaces: Moderately pubescent; matte. Color, upper and lower surfaces: Close to 144A; proximally, strongly tinged with close to 183C to 183D.

*Stipules*.—Quantity and arrangement: One at the base of the petiole. Length: About 3.8 cm. Width: About 4 mm. Shape: Lanceolate. Color, upper and lower surfaces: Close to 143A; towards the base, close to 183C to 183D.

Flower description:

*Flower appearance and arrangement*.—Single large papilionaceous flowers arranged in dense terminal racemes; freely flowering habit with usually about 200 flowers developing per inflorescence; flowers face mostly outwardly.

*Natural flowering season*.—Continuous flowering from early summer into the midsummer in The Netherlands.

*Flower longevity*.—Flowers last about two weeks on the plant; flowers not persistent.

*Fragrance*.—Strongly fragrant; peppery.

*Inflorescence height*.—About 62.9 cm.

*Inflorescence diameter*.—About 7.3 cm.

*Flower diameter*.—About 1.6 cm by 2.4 cm.

*Flower length* (*height*).—About 2.5 cm.

*Flower buds*.—Length: About 1.7 cm. Diameter: About 8 mm. Shape: Ovate. Color: Base, close to 145B; proximally, close to between 95A and 103B; distally, close to 157A.

*Petals*.—Quantity per flower: Flowers papilionaceous with an upper standard petal, two lateral (wing) petals and a lower keel petal. Length: Upper standard petal: About 2.1 cm. Lateral petals: About 2.1 cm. Keel: About 1.8 cm. Width: Upper standard petal: About 1.6 cm. Lateral petals: About 1.3 cm. Keel: About 4 mm. Shape: Upper standard petal: Orbicular; folded backwards. Lateral petals: Obovate; curved and concave. Keel: Ovate; curved and folded. Apex: Upper standard petal: Shallowly emarginate. Lateral petals: Obtuse. Keel: Caudate. Margin, all petals: Entire. Texture and luster, upper and lower surfaces, all petals: Smooth, glabrous; matte. Color, when opening, upper surface: Upper standard petal: Close to 157B to 157C; towards the base, close to 1B to 1C; proximal margins, close to 102B. Lateral petals: Close to 94C. Keel: Close to 145D; apex, close to 203C. Color, when opening, lower surface: Upper standard petal: Close to 150C to 150D; proximal margins, close to 99B. Lateral petals: Close to between 93A and 94A. Keel: Close to 145D; apex, close to 203C. Color, fully opened, upper surface: Upper standard petal: Close to 155A; proximal margins, close to 94A; with development, ground color becoming closer to between 155A and 158D. Lateral petals: Close to 94B; with development, color becoming closer to 93A. Keel: Close to 92B; apex, close to between 103A and 203C; color does not change with development. Color, fully opened, lower surface: Upper standard petal: Close to 155A; proximal margins, close to 94A. Lateral petals: Close to between 95A and 96A, closest to 96A. Keel: Close to 92B; apex, close to between 103A and 203C.

*Sepals*.—Quantity per flower: Two. Length: About 6 mm. Width: About 4 mm. Shape: Ovate. Apex: Narrowly acute. Base: Cuneate. Margin: Entire. Texture and luster, upper and lower surfaces: Densely pubescent; slightly glossy. Color: When opening and fully opened, upper surface: Close to 144B to 144C tinged with close to 91B. When opening and fully opened, lower surface: Close to 145B tinged with close to 91B.

*Peduncles*.—Length: About 50.3 cm. Diameter: About 9 mm. Strength: Strong. Aspect: Mostly erect. Texture: Smooth, glabrous. Color: Close to 177A.

*Pedicels*.—Length: About 1 mm. Diameter: About 1.5 mm. Strength: Moderately strong. Aspect: About 80° from peduncle axis. Texture: Smooth, glabrous. Color: Close to N187B to N187C.

*Reproductive organs*.—Androecium: Quantity per flower: About ten. Filament length: About 4 mm to 9 mm. Filament color: Close to 145D. Anther length: About 2 mm. Anther shape: Narrowly oblong. Anther color: Close to N170A to N170B. Amount of pollen: Moderate. Pollen color: Close to 24A. Gynoecium: Quantity per flower: One. Pistil length: About 1.1 cm. Style length: About 1 cm. Style color: Close to 150D. Stigma shaped: Club-shaped, fringed. Stigma color: Close to 1C to 1D. Ovary color: Close to 149D.

*Fruits*.—Quantity per flower: One. Length: About 5.7 cm. Diameter: About 1.2 cm. Texture: Densely pubescent. Color: Close to between 139A and 147A.

*Seeds*.—Quantity per fruit: About nine. Length: About 5 mm. Diameter: About 2 mm. Color: Close to 200A.

Garden performance: Plants of the new Lupine have been observed to have good garden performance and to tolerate rain, wind, high temperatures of about 35° C. and to be hardy to USDA Hardiness Zone 5.

Pathogen & pest resistance: Plants of the new Lupine have not been observed to be resistant to pathogens and pests common to Lupine plants.

It is claimed:

1. A new and distinct Lupine plant named 'WCLKICA' as illustrated and described.

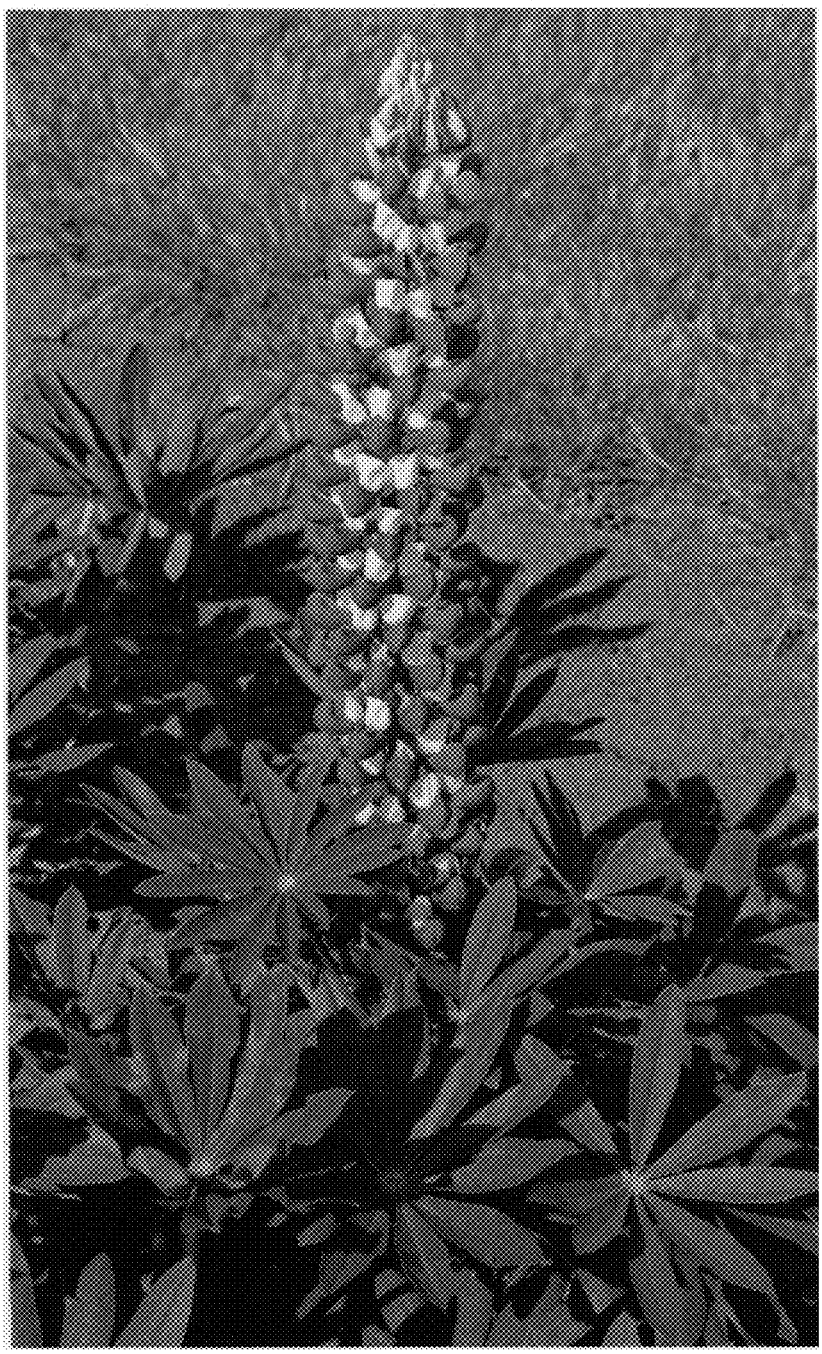

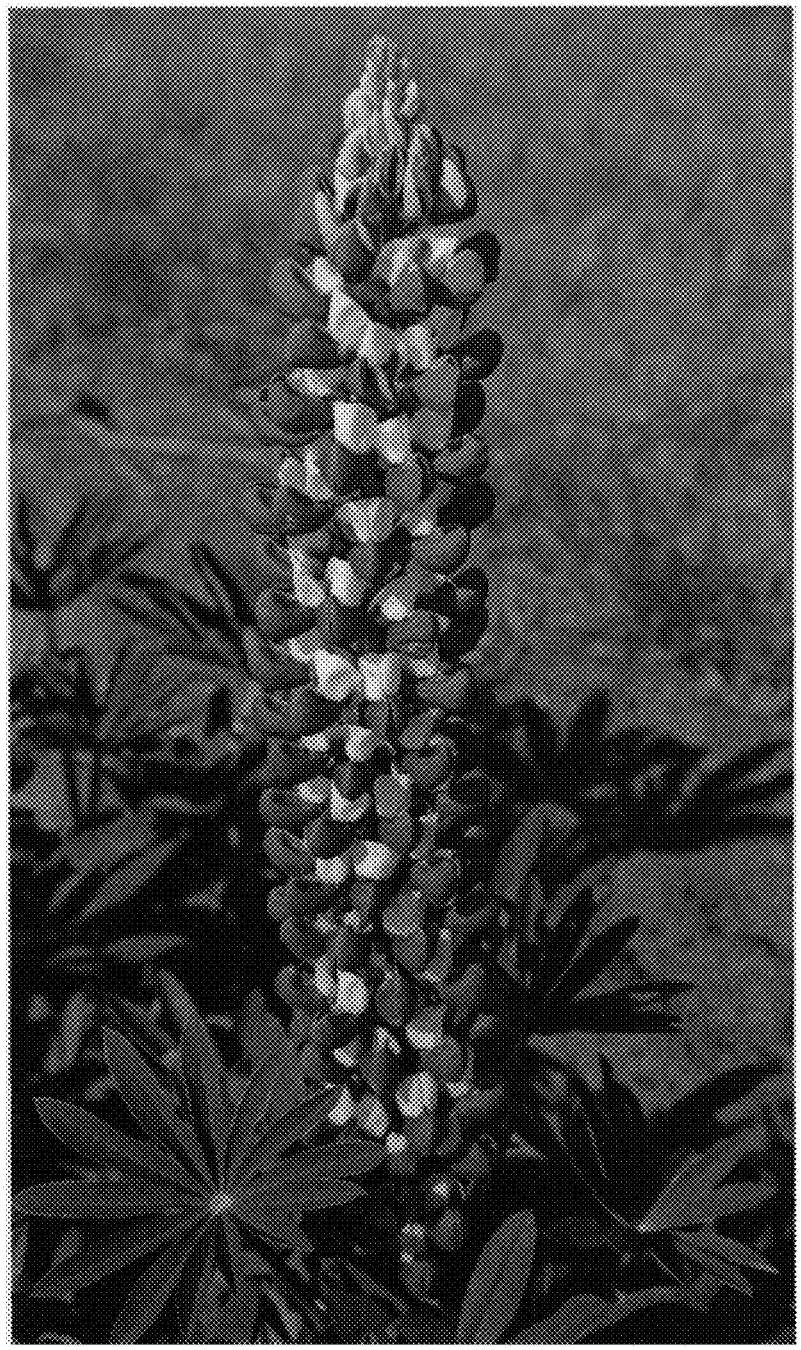

* * * * *